(12) United States Patent
Carney et al.

(10) Patent No.: US 8,172,395 B2
(45) Date of Patent: May 8, 2012

(54) MEDICAL DEVICES HAVING ANTIMICROBIAL COATINGS THEREON

(75) Inventors: Fiona Patricia Carney, Atlanta, GA (US); Manal M. Gabriel, Marietta, GA (US); Carol Ann Morris, Duluth, GA (US); John Martin Lally, Lilburn, GA (US)

(73) Assignee: Novartis AG, Basel (CH)

( * ) Notice: Subject to any disclaimer, the term of this patent is extended or adjusted under 35 U.S.C. 154(b) by 2529 days.

(21) Appl. No.: 10/722,256

(22) Filed: Nov. 25, 2003

(65) Prior Publication Data

US 2004/0135967 A1 Jul. 15, 2004

Related U.S. Application Data

(60) Provisional application No. 60/430,635, filed on Dec. 3, 2002.

(51) Int. Cl.
*G02C 7/02* (2006.01)
(52) U.S. Cl. ............................ 351/159; 264/1.7; 264/2.6
(58) Field of Classification Search .................. None
See application file for complete search history.

(56) References Cited

U.S. PATENT DOCUMENTS

| | | | | |
|---|---|---|---|---|
| 4,933,410 A * | 6/1990 | Okrongly | ................... | 525/333.6 |
| 5,171,318 A | 12/1992 | Gibson | | |
| 5,213,801 A * | 5/1993 | Sakuma et al. | ............... | 424/429 |
| 6,171,287 B1 * | 1/2001 | Lynn et al. | ..................... | 604/256 |
| 2001/0045676 A1 * | 11/2001 | Winterton et al. | ............. | 264/2.5 |

FOREIGN PATENT DOCUMENTS

| | | |
|---|---|---|
| EP | 0 611 782 | 5/1997 |
| EP | 0 537 774 | 1/1998 |
| WO | WO 80/02840 | 12/1980 |
| WO | WO 92/15198 | 9/1992 |
| WO | WO 99/35520 | 7/1999 |
| WO | WO 00/71175 | 11/2000 |
| WO | WO 01/56627 | 8/2001 |
| WO | WO 01/57118 | 8/2001 |
| WO | WO 01/92924 | 12/2001 |
| WO | WO 02/40536 | 5/2002 |
| WO | WO 02/064183 | 8/2002 |
| WO | 02092143 A1 | 11/2002 |
| WO | 02094331 A1 | 11/2002 |

OTHER PUBLICATIONS

Diaz-Achirica, et al, Permeabilization of the Mitonchondrial Inner Membrane by Short Cecropin-A-Melitin Hybrid Peptides, May 20, 1994, Eur. J. Biochem, 224,257-263.*
Authors: Padmaja Juwadi, Satyanarayana Vunnam, Elizabeth C. Merrifield, Hans G. Boman and R.B. Merrifield Title of Article: Hydrophobic Effects on Antibacterial and Channel-forming Properties of Cecropin A-Melittin Hybrids Published in: Journal of Peptide Science, 1996 vol. 2, pp. 223-232.
Authors: Satyanarayana Vunnam, Padmaja Juwadi, Kenneth S. Rotondi and R.B. Merrifield Title of Article: Synthesis and study of normal, enantio, retro, and retroenantio isomers of cecropin A-melittin hybrids, their end group effects and selective enzyme inactivation Published in: Journal of Peptide Research, 1998; 51(1), pp. 38-44.
Authors: Kevin L Piers, Melissa H. Brown and Robert E.W. Hancock Title of Article: Improvement of Outer Membrane-Permeabilizing and Lipopolysaccharide-Binding Activities of an Antimicrobial Cationic Peptide by C-Terminal Modification Published in: Antimicrobial Agents and Chemotherapy, Oct. 1994, vol. 38, No. 10, pp. 2311-2316.
Authors: K.L. Piers and R.E.W. Hancock Title of Article: The interaction of a recombinant cecropin/melittin hybrid peptide with the outer membrane of *Pseudomonas aeruginosa* Published in: Molecular Microbiology, 1994 12(6), pp. 951-958.
Authors: A. Giacometti, O. Cirioni, F. Barchiesi, M. Fortuna and G. Scalise Title of Article: In-vitro activity of cationic peptides alone and in combination with clinically used antimicrobial agents against *Pseudomonas aeruginosa* Published in: Journal of Antimicrobial Chemotheraphy, 1999, 44, pp. 641-645.
Authors: Hong Yan and Robert E.W. Hancock Title of Article: Synergistic Interactions between Mammalian Antimicrobial Defense Peptides Published in: Antimicrobial Agents and Chemotherapy, May 2001, vol. 45, No. 5, pp. 1558-1560,.
Authors: Andrea Giacometti, et al. Title of Article: Combination studies between polycationic peptides and clinically used antibiotics against Gram positive and Gram-negative bacteria Published in: Peptides, 2000, vol. 21, Issue 8, pp. 1155-1160.
Authors: Sharon L. Haynie, et al. Title of Article: Antimicrobial Activities of Amphiphilic Peptides Covalently Bonded to a Water-Insoluble Resin Published in: Antimicrobial Agents and Chemotherapy, Feb. 1995, vol. 39, No. 2, pp. 301-307.
Authors: David C. LaPorte et al. Title of Article: Inhibition of *Escherichia coli* Growth and Respiration by Polymyxin B Covalently Attached to Agarose Beads Published in: Biochemistry, 1977, vol. 16, No. 8, pp. 1642-1648.
Authors: Kenneth S. Rosenthal et al. Title of Article: Disruption of the *Escherichia coli* Outer Membrane Permeability Barrier by Immobilized Polymyxin B Published in: The Journal of Antibiotics, Dec. 1977, vol. 30, No. 12, pp. 1087-1092.
English Translation of Japan Office Action Notification of Reasons for Rejection, Dispatch No: 488660, Dispatch Date: Jul. 13, 2010, Japanese Patent Application No: 2004-556275.
English Translation of Japan Office Action Notification of Reasons for Rejection, Dispatch No: 009598, Dispatch Date: Jan. 11, 2011, Japanese Patent Application No: 2004-556275.

* cited by examiner

*Primary Examiner* — Walter Webb
(74) *Attorney, Agent, or Firm* — Sheng-Hsin Hu; Jian Zhou

(57) ABSTRACT

The present invention provides a medical device, preferably a contact lens, which comprises an antimicrobial LbL coating containing one or more antimicrobial pepetides. The antimicrobial coating of the invention can impart to the medical an increased surface hydrophilicity and a relatively high antimicrobial activity coupled with low cytotoxicity. The antimicrobial coating of the invention has a minimal adverse effects on the desirable bulk properties of a contact lens, such as oxygen permeability, ion permeability, and optical properties. An antimicrobial coating of the present invention may find particular use in extended-wear contact lenses. In addition, the invention provides a method for making a medical device, preferably a contact lens, having an antimicrobial LbL coating thereon.

5 Claims, No Drawings

MEDICAL DEVICES HAVING ANTIMICROBIAL COATINGS THEREON

This application claims under 35 USC §119 (e) the benefit of the filing date of U.S. Provisional Application Serial No. 60/430,635 filed Dec. 3, 2002 and all references incorporated therein.

The present invention generally relates to a medical device having an antimicrobial coating thereon. In particular, the present invention relates to a medical device having an antimicrobial LbL coating which is not covalently attached to the medical device and comprises one or more antimicrobial peptides, or, to a medical device having a layer of one or more antimicrobial peptides covalently attached to the medical device. In addition, this invention provides a method for making a medical device having an antimicrobial coating.

BACKGROUND

Contact lenses are often exposed to one or more microorganisms during wear, storage and handling. They can provide surfaces onto which the microorganisms can adhere and then proliferate to form a colony. Microbial adherence to and colonization of contact lenses may enable microorganisms to proliferate and to be retained at the ocular surface for prolonged periods and thereby may cause infection or other deleterious effects on the ocular health of the eye in which the lens is used. Therefore, it is desirous to make various efforts to minimize and/or eliminate the potential for microorganism adhesion to and colonization of contact lenses.

Many attempts have been made to develop antimicrobial medical devices. Two approaches have been proposed. One approach is to incorporate antimicrobial compounds into a polymeric composition for molding a contact lens. For example, Chalkley et al. in Am. J. Ophthalmology 1966, 61:866-869, disclosed that germicidal agents were incorporated into contact lenses. U.S. Pat. No. 4,472,327 discloses that antimicrobial agents may be added to the monomer before polymerization and locked into the polymeric structure of the lens. U.S. Pat. Nos. 5,358,688 and 5,536,861 disclose that contact lenses having antimicrobial properties may be made from quaternary ammonium group containing organosilicone polymers. European patent application EP0604369 discloses that deposit-resistant contact lenses can be prepared from hydrophilic copolymers that are based on 2-hydroxyethyl methacrylate and comonomers containing a quaternary ammonium moiety. Another example is an ocular lens material, disclosed in European patent application EP0947856A2, which comprises a quaternary phosphonium group-containing polymer. A further example is U.S. Pat. No. 5,515,117 which discloses contact lenses and contact lens cases made from materials which comprise polymeric materials and effective antimicrobial components. A still further example is U.S. Pat. No. 5,213,801 which discloses contact lenses made from materials comprising a hydrogel and an antimicrobial ceramic containing at least one metal selected from Ag, Cu and Zn. There are some disadvantages associated with this approach for making antimicrobial contact lenses. First, polymeric compositions having antimicrobial properties may not possess all properties desired for contact lenses, especially extended-wear contact lenses, which hinders their practice uses. Second, antimicrobial compounds may exhibit greatly diminished activity since they may not be in contact with microorganisms adhered to the surface of contact lens.

The other approach for making antimicrobial medical devices is to form antimicrobial coatings, containing leachable or covalently attached antimicrobial agents, on medical devices. Antimicrobial coatings containing leachable antimicrobial agents may not be able to provide antimicrobial activity over the period of time when used in the area of the human body. In contrast, antimicrobial coating containing covalently bound antimicrobial agents can provide antimicrobial activity over a relatively longer period of time. However, antimicrobial compounds in such coatings may exhibit greatly diminished activity when comparing the activity of the unbound corresponding antimicrobial compounds in solution, unless assisted by hydrolytic breakdown of either the bound antimicrobial compounds or the coating itself.

Currently, a wide variety of antimicrobial agents have been proposed to be used as coatings for contact lenses (see, for example, U.S. Pat. No. 5,328,954). Prior known antimicrobial coatings include antibiotics, lactoferrin, metal chelating agents, substituted and unsubstituted polyhydric phenols, amino phenols, alcohols, acid and amine derivatives, and quaternary ammonium group-containing compounds. However, such antimicrobial coatings have disadvantages and are unsatisfactory. The overuse of antibiotics can lead to proliferation of antibiotic-resistant microorganisms. Other coatings may not have broad spectrum antimicrobial activity, may produce ocular toxicity or allergic reactions, or may adversely affect lens properties required for ensuring corneal health and for providing the patient with good vision and comfort.

Therefore, there is a need for antimicrobial coatings that can provide high bactericidal efficacy and broad spectrum antimicrobial activity coupled with low cytotoxicity. There is also a need for new contact lenses having antimicrobial coatings, which have high bactericidal efficacy, a broad spectrum of antimicrobial activities, and minimal adverse effects on the wearer's ocular health and comfort. Such contact lenses may have increased safety as extended-wear contact lenses which could provide comfort, convenience, and safety.

Moreover, surgical and device related infection remains to be one of the main clinical and economic challenges in the field of medical devices and in health care industry in general. Each year, as many as 2 million hospital patients in the United States develop nosocomial infections, and approximately 80% of the 80,000 annual deaths due to nosocomial infections are device-related. A potent and cost-effective antimicrobial coating for medical devices would be a key to mitigate the infection-related clinical challenges and economic burden of health care.

One object of the invention is to provide an antimicrobial coating which has a high antimicrobial efficacy coupled with low cytotoxicity.

Another object of the invention is to provide a medical device having an antimicrobial coating that has a high antimicrobial efficacy coupled with low cytotoxicity.

A further object of the invention is to provide a cost-effective and efficient process for forming an antimicrobial coating on a medical device.

SUMMARY OF THE INVENTION

These and other objects of the invention are met by the various aspects of the invention described herein.

The invention, in one aspect, provides a medical device comprising: an LbL coating that is not covalently attached to the medical device, wherein the LbL coating is composed of (i) at least one layer of a first polyionic material or (ii) at least one layer of the first polyionic material which is not covalently attached to the surface of the medical device and at least one layer of a second polyionic material having charges opposite of the charges of the first polyionic material, wherein said first and second polyionic materials, independently of each other, have functional groups which provide reactive sites; and a peptide layer of one or more antimicrobial peptides which are covalently attached to the LbL coating through the reactive sites.

The invention in another aspect, provides a medical device having an antimicrobial LbL coating that is not covalently attached to the medical device, wherein the antimicrobial coating comprises: (i) at least one cationic layer of a mixture including a positively-charged polyionic material and at least one antimicrobial peptide; (ii) at least one anionic layer of a negatively charged polyionic material.

The invention, in still another aspect, provides a medical device comprises a layer of at least one antimicrobial peptide covaletly attached to the medical device.

The invention, in a further aspect, provides a method for forming an antimicrobial LbL coating on a medical device, comprising the steps of: a) applying an LbL coating onto the surface of the medical device, wherein the LbL coating is composed of (i) at least one layer of a first polyionic material which is not covalently attached to the surface of the medical device or (ii) at least one layer of the first polyionic material which is not covalently attached to the surface of the medical device and at least one layer of a second polyionic material having charges opposite of the charges of the first polyionic material, wherein said first and second polyionic materials, independently of each other, have functional groups which provide reactive sites; and b) covalently attaching a layer of at least one antimicrobial peptide onto the LbL coating through said reactive sites.

The invention, in another further aspect, provides a method for forming an antimicrobial LbL coating on a medical device. The method comprises alternatively applying one positively-charged layer of a mixture including a polycationic material and at least one antimicrobial peptide and one negatively-charged layer of a polyanionic material onto a medical device to form the antimicrobial LbL coating.

The invention, in still a further aspect, provides a method for forming an antimicrobial LbL coating on a medical device. The method comprises functionalizing the surface of the medical device to provide reactive sites and covalently attaching a layer of at least one antimicrobial peptide onto the medical device through said reactive sites.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

An "article" refers to an ophthalmic lens, a mold for making an ophthalmic lens, or a medical device other than ophthalmic lens.

A "medical device", as used herein, refers to a device or a part thereof having one or more surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices. In a preferred embodiment, medical devices are ophthalmic devices; and (7) cases or containers for storing ophthalmic devices or ophthalmic solutions.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Biocompatible", as used herein, refers to a material or surface of a material, which may be in intimate contact with tissue, blood, or other bodily fluids of a patient for an extended period of time without significantly damaging the ocular environment and without significant user discomfort.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Surface modification", as used herein, refers to treating an article to alter its surface properties. For example, the surface modification of a contact lens includes, without limitation, the grafting of monomers or macromers onto polymers to make the lens biocompatible, deposit resistant, more hydrophilic, more hydrophobic, or the deposing of polyionic materials (LbL coating) to increase the lens hydrophilic properties or to impart antimicrobial or antifungal properties.

"LbL coating", as used herein, refers to a coating that is not covalently attached to a medical device and is obtained through a layer-by-layer ("LbL") deposition of polyionic materials on an article. Any suitable LbL polyelectrolyte deposition techniques can be used in the LbL coating. For example, a pending U.S. patent application Ser. No. 09/199, 609, filed on Nov. 25, 1998, discloses an LbL polyelectrolyte deposition technique that involves consecutively dipping a substrate into oppositely charged polyionic materials until a coating of a desired thickness is formed.

As used herein, "asymmetrical coatings" on an ophthalmic lens refers to the different coatings on the first surface and the opposite second surface of the ophthalmic lens. As used herein, "different coatings" refers to two coatings that have different surface properties or functionalities.

The term "bilayer" is employed herein in a broad sense and is intended to encompass, a coating structure formed by applying one layer of a first polyionic material and subsequently one layer of a second polyionic material having charges opposite of the charges of the first polyionic material. It should be understood that the layers of the first and second polyionic materials may be intertwined with each other in the bilayer.

An "innermost layer", as used herein, refers to the first layer of an LbL coating, which is applied onto the surface of a medical device.

A "capping layer", as used herein, refers to the last layer of a coating material which is applied onto the surface of a medical device.

A "polyquat", as used herein, refers to a polymeric quaternary ammonium group-containing compound.

A "charged polymeric material" or a "polyionic material" refers to a charged polymer that has a plurality of charged groups in a solution, or a mixture of charged polymers each of which has a plurality of charged groups in a solution. Exemplary charged polymers includes polyelectrolytes, p- and n-type doped conducting polymers. Charged polymeric materials include both polycationic (having positive charges) and polyanionic (having negative charges) polymeric materials.

An "antimicrobial agent", as used herein, refers to a chemical that is capable of decreasing or eliminating or inhibiting the growth of microorganisms such as that term is known in the art.

An "averaged value of coefficient of friction" refers to a value of coefficient of friction, which is obtained by averaging measurements of at least 3 individual medical devices.

An "averaged contact angle" refers to a contact angle (Sessile Drop), which is obtained by averaging measurements of at least 3 individual medical devices.

As used herein, "increased surface hydrophilicity" or "increased hydrophilicity" in reference to a coated ophthalmic device means that the coated ophthalmic device has a reduced averaged contact angle compared with an uncoated ophthalmic device.

The terms "polypeptide", "peptide", or "protein" are used interchangeably herein to designate a linear series of amino acid residues connected one to the other by peptide bonds between the alpha-amino and carboxy groups of adjacent residues. Sequences are conventionally given from the amino terminus to the carboxyl terminus. Component amino acids may be of the D- or the L-configuration. Unless otherwise noted, the amino acids are L-amino acids. When all component amino acids are of L-configuration, the peptide is said to be an L-enantiomer. When all the amino acids in a peptide are in the D-configuration, that peptide is said to be a D-enantiomer.

"Amino acid" is used in its broadest sense to include naturally occurring amino acids as well as non-naturally occurring amino acids including amino acid analogs. In view of this broad definition, one skilled in the art would know that reference herein to an amino acid includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway.

The term "conservative substitution" is used in reference to proteins or peptides to reflect amino acid substitutions that do not substantially alter the activity (e.g., antimicrobial activity) of the molecule. Typically conservative amino acid substitutions involve substitution one amino acid for another amino acid with similar chemical properties (e.g., charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (1), Leucine (L), Methionine (M), Valine (V); and 6) Phenylalanine (F), Tyrosine (Y), Tryptophan (W).

The designations of amino acid residues referred to herein, as recommended by the IUPAC-IUB Biochemical Nomenclature Commission, are list in Table 1.

TABLE 1

| Amino Acid | Symbol | |
| --- | --- | --- |
| | Three-Letter | One-letter |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"MIC" (minimal inhibitory concentration) is the minimum concentration required to prevent growth of bacterial cells in liquid medium.

In general, the present invention is directed to a medical device, preferably an ophthalmic device, more preferably a contact lens, having a core material and an antimicrobial LbL coating formed thereon as well as to a method for making the same.

In accordance with the present invention, the core material of a medical device may be any of a wide variety of polymeric materials. Exemplary core materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids.

A preferred group of core materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefins, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred core materials to be coated is amphiphilic-segmented copolymers comprising at least one hydrophobic segment and at least one hydrophilic segment, which are linked through a bond or a bridge member. Examples are silicone hydrogels, for example those disclosed in PCT applications WO 96/31792 to Nicolson et al. and WO 97/49740 to Hirt et al.

A particular preferred group of core materials to be coated comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The core material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

Moreover, the core material to be coated may also be an inorganic or metallic base material without suitable reactive groups, e.g. ceramic, quartz, or metals, such as silicon or gold, or other polymeric or non-polymeric substrates. e.g., for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The core material to be coated can be subjected a surface modification before applying an antimicrobial coating.

The form of the core material to be coated may vary within wide limits. Examples are particles, granules, capsules, fibers, tubes, films or membranes, preferably moldings of all kinds such as ophthalmic moldings, for example intraocular lenses, artificial cornea or in particular contact lenses.

An antimicrobial coating of the invention can provide an increased surface hydrophilicity and a relatively high antimicrobial activity coupled with low cytotoxicity. It has a minimal adverse effects on the desirable bulk properties of the lens, such as oxygen permeability, ion permeability, and optical properties. An antimicrobial coating of the present invention may find particular use in extended-wear contact lenses.

In accordance with one aspect of the invention, an antimicrobial coating of the invention comprises: an LbL coating that is not covalently attached to the medical device, wherein the LbL coating is composed of (i) at least one layer of a first polyionic material or (ii) at least one layer of the first polyionic material which is not covalently attached to the surface of the medical device and at least one layer of a second polyionic material having charges opposite of the charges of the first polyionic material, wherein said first and second polyionic materials, independently of each other, have functional groups which provide reactive sites; and an peptide layer of one or more antimicrobial peptides which are covalently attached to the LbL coating through the reactive sites.

In accordance with another aspect of the invention, an antimicrobial coating of the invention comprises: (i) at least one cationic layer of a mixture including a positively-charged polyionic material and at least one antimicrobial peptide; (ii) at least one anionic layer of a negatively charged polyionic material.

Antimicrobial peptides have common structural features, including a net cationic charge due to the presence of multiple charged residues (Arg, Lys), the presence of multiple cysteine residues, and in most cases the ability to form amphipathic structures. The antimicrobial peptides can be subdivided into a number of groups based on their amino acid content, structure and source. Several reviews of several classes of these peptides have been recently published (See, for example, Lehrer & Ganz (1966) AnnaL N.Y Acad Sci., 797:228-239; Maloy & Kari (1995) Biopolymers, 37:105-122).

In accordance with the present invention, any known antimicrobial peptides, which have relatively effective antimicrobial activities while have low cytotoxicity, can be used in the invention. An antimicrobial peptide can be one selected from the group consisting of Cecropin A melittin hybrid, indolicidin, lactoferricin, Defensin 1, Bactenecin (bovin), Magainin 2, functionally equivalent or superior analogs thereof, mutacin 1140, and mixtures thereof. The antimicrobial peptide can have a —COOH or $NH_2$ group in the C-terminal of the peptide. Preferably, an anitmicrobial peptide is Cecropin A-melittin hybrid or indolicidin.

"Functionally equivalent or superior analogs" of an antimicrobial peptide refers to derivatives of a native antimicrobial peptide in which one or more amino acid residues have been replaced by a different amino acid (conservative amino acid substitution or others) or deleted or inserted to provide equal or better biological activity (i.e., antimicrobial activity). A functionally equivalent or superior analog can be a substitution analog, a deletion analog, or an addition analog.

A substitution analog is a peptide in which one or more amino acid residues have been replaced by a different amino acid (conservative amino acid substitution or others) to provide equal or better biological activity (i.e., antimicrobial activity). A deletion analog is a peptide in which one or more amino acid residues have been deleted to provide equal or better antimicrobial activity. An addition analog is peptide in which one or more amino acid residues have been inserted to provide equal or better biological activity (i.e., antimicrobial activity). A person skilled in the art will know how to design and prepare a substitution analog. For example, U.S. Pat. Nos. 5,792,831 and 5,912,231 (herein incorporated by reference in their entireties) describe substitution and deletion analogs of Magainin 2.

Antimicrobial peptides can be obtained from commercial suppliers or can be synthesized according to any known suitable method, for example, using an Applied Biosystems Model 430A peptide synthesizer. It is understood in the art that there are other suitable peptide synthetic devices or that manual peptide synthesis could be carried out to produce the peptides of the present invention. Automated solid phase peptide synthesis is described, e.g., in Stewart et al. (1984) Solid Phase Peptide Synthesis, Pierce Chemical Company, Rockford, Ill.).

It is known to a person skilled in the art that an anitmicrobial peptide can be produced by expression in a suitable bacterial or eukaryotic host. Suitable methods for expression are described by Sambrook, et al., (In: *Molecular Cloning, A Laboratory Manual, 2nd Edition, Cold Spring Harbor Press*, Cold Spring Harbor, N.Y. (1989)), or similar texts, herein incorporated by reference in its entirety.

The polyionic materials that may be employed in the present invention include polyanionic and polycationic polymers. Examples of suitable polyanionic polymers include, for example, a synthetic polymer, a biopolymer or modified biopolymer comprising carboxy, sulfo, sulfato, phosphono or phosphato groups or a mixture thereof, or a salt thereof, for example, a biomedical acceptable salt and especially an ophthalmically acceptable salt thereof when the article to be coated is an ophthalmic device.

Examples of synthetic polyanionic polymers are: a linear polyacrylic acid (PAA), a branched polyacrylic acid, a polymethacrylic acid (PMA), a polyacrylic acid or polymethacrylic acid copolymer, a maleic or fumaric acid copolymer, a poly(styrenesulfonic acid) (PSS), a polyamido acid, a carboxy-terminated polymer of a diamine and a di- or polycarboxylic acid (e.g., carboxy-terminated Starburst™ PAMAM dendrimers from Aldrich), a poly(2-acrylamido-2-methylpropanesulfonic acid) (poly-(AMPS)), an alkylene polyphosphate, an alkylene polyphosphonate, a carbohydrate polyphosphate or carbohydrate polyphosphonate (e.g., a teichoic acid). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone. Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Polycationic polymers comprising primary or secondary amino groups or a salt thereof are preferred.

Examples of synthetic polycationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$-$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$-$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly(N,N-diallyl-N,N-di-$C_1$-$C_4$-alkyl-ammoniumhalide);
(viii) a homo- or copolymer of a quaternized di-$C_1$-$C_4$-alkyl-aminoethyl acrylate or methacrylate, for example a poly(2-hydroxy-3-methacryloylpropyltri-$C_1$-$C_2$-alkylammonium salt) homopolymer such as a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) polyquat; or
(x) a polyaminoamide (PAMAM), for example a linear PAMAM or a PAMAM dendrimer such as an amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Examples of polycationic biopolymers or modified biopolymers that may be employed in the bilayer of the present invention include: basic peptides, proteins or glucoproteins, for example, a poly-ε-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (II); a polyvinylamine homo- or -copolymer or a polyethyleneimine homopolymer, in particular a polyallylamine or polyethyleneimine homopolymer, or a poly(vinylamine-co-acrylamid) copolymer.

The foregoing lists are intended to be exemplary, but clearly are not exhaustive. A person skilled in the art, given the disclosure and teaching herein, would be able to select a number of other useful polyionic materials.

It has been discovered and disclosed in U.S. application Ser. No. 09/005,317 that complex and time-consuming pretreatment of a core material (medical device) is not required prior to binding of a polyionic material to the core material. By simply contacting a core material of a medical device, for example, a contact lens, with one or more solutions each containing one or more polyionic materials, an LbL coating can be formed on a medical device to modify the surface properties of the core material of the medical device. An LbL coating can be a single layer or a bilayer or multiple bilayers.

A preferred number of bilayers in an antimicrobial LbL coating of the invention are about 5 to about 20 bilayers. While more than 20 bilayers are possible, it has been found that delamination may occur in some LbL coatings having an excessive number of bilayers.

An antimicrobial LbL coating of the invention can be formed from at least one polyionic material, preferably two polyionic materials having charges opposite to each other.

An antimicrobial LbL coating of the invention preferably comprises at least one layer of a lubricious coating material which is selected from the group consisting of PAMAM dendrimers, PAAm-co-PAA, PVP-co-PM, glycosaminoglycanes, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides, glucoproteins, and aminoalkylated polysaccharides.

An antimicrobial LbL coating of the invention preferably comprise at least one layer of a polyquat which has antimicrobial activities.

Application of an LbL coating may be accomplished in a number of ways as described in pending U.S. patent applications (application Ser. Nos. 09/005,317, 09/774,942, 09/775,104), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

For example, a solely dip-coating process involves the steps of: (a) immersing a medical device in a first coating solution of a first polyionic material; (b) optionally rinsing the medical device by immersing the medical device in a first rinsing solution; (c) immersing said medical device in a second coating solution of a second polyionic material to form a first polyelectrolyte bilayer of the first and second polyionic materials, wherein the second polyionic material has charges opposite of the charges of the first polyionic material; (d) optionally rinsing said medical device by immersing the medical device in the rinsing solution; and (e) optionally repeating steps (a) to (d) for a number of times to form additional polyelectrolyte bilayers. A thicker LbL coating can be produced by repeating steps (a) to (d) preferably for 2 to 40 times. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. For example, a solely spray-coating process generally includes the steps of: (a) spraying a medical device with a first coating solution of a first polyionic material; (b) optionally rinsing the medical device by spraying it with a rinsing solution; (c) spraying said medical device with a second coating solution of a second polyionic material to form a first polyelectrolyte bilayer of the first and second polyionic materials, wherein the second polyionic material has charges opposite of the charges of the first polyionic material; (d) optionally rinsing said medical device by spraying it with the rinsing solution; (e) optionally repeating steps (a) to (d) for a number of times. A thicker LbL coating can be produced by repeating steps (a) to (d) preferably for 2 to 40 times.

The spray coating application may be accomplished via a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. Application No. 60/312,199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

However, where a coating solution containing a first polyionic material is used to form an innermost layer of a biocompatible LbL coating of the invention on the surface of a medical device, it is desirable that the concentration of the first charged polymeric material in the solution is sufficiently high enough to increase the hydrophilicity of the LbL coating. Preferably, the concentration of the charged polymeric material in a solution for forming the innermost layer of an LbL coating is at least three folder higher than the concentration of a coating material in a coating solution for forming subsequent layers of the LbL coating. More preferably, the concentration of the charged polymeric material in a solution for forming the innermost layer of an LbL coating is at least ten folder higher than the concentration of a coating material in a coating solution for forming subsequent layers of the LbL coating.

Polycationic solutions can also be formed in a manner as described above. For example, in one embodiment, poly(allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

In some embodiments of the present invention, it may be desirable to use a solution containing both polyanionic and polycationic materials within a single solution. For example, a polyanionic solution can be formed as described above, and then mixed with a polycationic solution that is also formed as described above. In one embodiment, the solutions can then be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

In order to alter various characteristics of the coating, such as thickness, the molecular weight of the polyionic materials including polyquats can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In addition to polyionic and non-charged polymeric materials, a coating solution for forming the bilayer or part of it, can also contain additives. As used herein, an additive can generally include any chemical or material. For example, active agents, such as antimicrobials and/or antibacterials can be added to a solution forming the bilayer, particularly when used in biomedical applications. Some antimicrobial polyionic materials include polyquaternary ammonium compounds, such as those described in U.S. Pat. No. 3,931,319 to Green et al. (e.g. POLYQUAD®).

Moreover, other examples of materials that can be added to a coating solution are polyionic materials useful for ophthalmic lenses, such as materials having radiation absorbing properties. Such materials can include, for example, visibility-tinting agents, iris color modifying dyes, and ultraviolet (UV) light tinting dyes.

Still another example of a material that can be added to a coating solution is a polyionic material that inhibits or induces cell growth. Cell growth inhibitors can be useful in devices that are exposed to human tissue for an extended time with an ultimate intention to remove (e.g. catheters or Intra Ocular Lenses (IOL's), where cell overgrowth is undesirable), while cell growth-inducing polyionic materials can be useful in permanent implant devices (e.g. artificial cornea).

When additives are applied to a coating solution, such additives, preferably, have a charge. By having a positive or negative charge, the additive can be substituted for the polyionic material in solution at the same molar ratio. For example, polyquaternary ammonium compounds typically have a positive charge. As such, these compounds can be substituted into a solution of the present invention for the polycationic component such that the additive is applied to the core material of an article in a manner similar to how a polycationic would be applied.

A medical device, which comprises an LbL coating that is not covalently attached to the medical device and an peptide layer of at least one antimicrobial peptides which are covalently attached to the LbL coating through the reactive sites of the LbL coating, can be made by first applying an LbL coating to a preformed medical device according to one of the above-described coating methods using at least one polyionic material having functional groups which will be served as reactive sites and then by covalently attaching a peptide layer of at least one antimicrobial peptide to some of those reactive sites.

Antimicrobial peptides can be bound covalently to the LbL coating. This may be either a direct reaction or, preferably, a reaction in which a coupling agent is used. For example, a direct reaction may be accomplished by the use of a reagent of reaction that activates a group in the LbL coating or the antimicrobial peptide making it reactive with a functional group on the peptide or LbL coating, respectively, without the incorporation of a coupling agent. For example, one or more amine groups on the peptide may be reacted directly with isothiocyanate, acyl azide, N-hydroxysuccinimide ester, sulfonyl chloride, an aldehyde, glyoxal epoxide, 25 carbonate, aryl halide, imido ester, or an anhydride group in the LbL coating.

Alternatively, coupling agents may be used. Coupling agents useful for coupling antimicrobial peptide to the LbL coating of a medical device include, without limitation, N. N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl)carbodiimide, diisopropyl carbodiimide, or mixtures thereof. The carbodiimides also may be used with N-hydroxysuccinimide or N-hydroxysulfosuccinimide to form esters that can react with amines to form amides.

Amino groups also may be coupled to the LbL coating by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis(succinimidylpropionate), 3,3'-dithiobis(sulfosuccinimidylpropionate), disuccinimidyl suberate, bis(sulfosuccinimidyl) suberate, disuccinimidyl tartarate and the like, imidoesters, including, without limitation, dimethyl adipimate, difluorobenzene derivatives, including without limitation 1,5-difluoro-2,4 dinitrobenzene, bromofunctional aldehydes, including without limitation gluteraldehyde, and his epoxides, including without limitation 1,4-butanediol diglycidyl ether. One ordinarily skilled in the art will recognize that any number of other coupling agents may be used depending on the functional groups present in the LbL coating.

A medical device having an antimicrobial LbL coating, which is not covalently attached to the medical device and comprises at least one cationic layer of a mixture including a positively-charged polyionic material and at least one antimicrobial peptide and at least one anionic layer of a negatively charged polyionic material, can be prepared by applying alternatively one cationic layer of a mixture including a positively-charged polyionic material and at least one antimicrobial peptide and one anionic layer of a negatively charged polyionic material, onto a preformed medical device according to one of the above-described coating methods.

Alternatively, such medical device can also be made by first applying an antimicrobial coating, which is not covalently attached to the medical device and comprises at least one cationic layer of a mixture including a positively-charged polyionic material and at least one antimicrobial peptide and at least one anionic layer of a negatively charged polyionic material, onto a mold for making a medical device and then transfer-grafting the antimicrobial coating to the medical device made from the mold, in substantial accordance with the teachings of U.S. patent application (Ser. No. 09/774,942), herein incorporated by reference in its entirety.

An LbL coating of the present invention may find particular use in extended-wear contact lenses. The LbL coating of the invention may have a minimal adverse effects on the desirable bulk properties of the lens, such as oxygen permeability, ion permeability, and optical properties.

The invention is also related to a medical device having a layer of at least one antimicrobial peptide covaletly attached to the medical device and method for making the same.

Such medical device can be prepared by first functionalizing the surface of a preformed medical device to obtain function groups and then covalently attaching a layer of antimicrobial peptides. Surface modification (or functionalization) of a medical device is well known to a person skilled in the art. Any known suitable method can be used.

For example, the surface modification of a contact lens includes, without limitation, the grafting of monomers or macromers onto polymers to make the lens biocompatible, wherein monomers or macromers contain functional groups, for example, such as hydroxyl group, amine group, amide group, sulfhydryl group, —COOR(R and R' are hydrogen or $C_1$ to $C_8$ alkyl groups), halide (chloride, bromide, iodide), acyl chloride, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, hydroxysuccinimide ester, hydroxysulfosuccinimide ester, imido ester, hydrazine, axidonitrophenyl group, azide, 3-(2-pyridyl dithio)proprionamide, glyoxal, aldehyde, epoxy.

It is well known in the art that a pair of matching functional groups can form a covalent bond or linkage under known reaction conditions, such as, oxidation-reduction conditions, dehydration condensation conditions, addition conditions, substitution (or displacement) conditions, 2+2 cyclo-addition conditions, Diels-Alder reaction conditions, ROMP (Ring Opening Metathesis Polymerization) conditions, vulcanization conditions, cationic crosslinking conditions, and epoxy hardening conditions. For example, an amino group is covalently bondable with aldehyde (Schiff base which is formed from aldehyde group and amino group may further be reduced); an hydroxyl group and an amino group are covalently bondable with carboxyl group; carboxyl group and a sulfo group are covalently bondable with hydroxyl group; a mercapto group is covalently bondable with amino group; or a carbon-carbon double bond is covalently bondable with another carbon-carbon double bond.

Exemplary covalent bonds or linkage, which are formed between pairs of crosslinkable groups, include without limitation, ester, ether, acetal, ketal, vinyl ether, carbamate, urea, amine, amide, enamine, imine, oxime, amidine, iminoester, carbonate, orthoester, phosphonate, phosphinate, sulfonate, sulfinate, sulfide, sulfate, disulfide, sulfinamide, sulfonamide, thioester, aryl, silane, siloxane, heterocycles, thiocarbonate, thiocarbamate, and phosphonamide.

Another example is amination of the surface of a medical device. If the surface of a core material has hydroxy groups, the medical device may be placed in a bath of an inert solvent, such as tetrahydrofuran, and tresyl chloride. The hydroxy groups on the surface are then tresylated. Once tresylated, the surface may be aminated in a water solution of ethylene diamine, which results in bonding the group —NH—$CH_2$—$CH_2$—$NH_2$ to the carbon atom thereon. Alternatively, for example, a contact lens made from a hydrogel, can be dipped into or sprayed with a solution containing a diaziridine compound, which is subsequently attached covalently to the surface of the contact lens via a thermal process, so as to functionalize the contact lens. Such functionalized lenses can be used in covalently attaching of a layer of antimicrobial peptides.

The previous disclosure will enable one having ordinary skill in the art to practice the invention. In order to better enable the reader to understand specific embodiments and the advantages thereof, reference to the following examples is suggested.

EXAMPLE 1

Peptide Screening by Inhibition Assays

Eight commercially available peptides (from American Peptides Company, Inc.) are screened for antimicrobial activity against four virulent ocular bacterial strains as follows.

A bacterial suspension of $10^8$ c.f.u. is made in phosphate buffered saline at pH 7.4. A 1 mL aliquot of each suspension is evenly dispersed over the surface of Mueller Hinton II Agar plates (2.0 g beef extract, 17.5 g acid hydrosylate of casein, 1.5 g starch, 17.0 g agar; Becton Dickinson, MD, USA). Holes with a diameter of about 5 mm are made in the plate and a 100 μl aliquot of each peptide (10 μg/mL solution) is placed in one of the holes. Solutions of both positive (broad spectrum antibiotics and Solocare) and negative controls (PBS) are also placed on each plate to ensure that the bacteria is viable. The plate is then incubated at 35° C. overnight, and the zone of inhibition is monitored. Results (Table 2) of screening of the peptides for appropriate antibacterial activity show that Cecropin mellitin and Indolicidin appear to be better candidates for antimicrobial agents.

TABLE 2

| Antimicrobial agent (10 μg/mL) | Antimicrobial activities | | | |
|---|---|---|---|---|
| | Staph. epi | Strep. rattus | Ps. aeruginosa 9027 | Ps. aeruginosa GSU #3 |
| Antibiotic (+ Control) | ++++ | ++++ | +++ | +++ |
| Solocare (+ Control) | +++ | ++ | − | − |
| PBS (− Control) | − | − | − | − |
| Defensin 1 (HNP-1) | + | − | − | − |
| Indolicidin | ++ | + | + | + |
| Lactoferricin | + | − | − | − |
| Cecropin A Melittin Hybrid | ++ | ++ | ++ | ++ |
| Bactenecin (bovine) | + | + | − | − |
| Magainin 2 | ++ | − | − | − |
| Nisin | − | − | − | − |
| Mutacin 1140 | ++ | ++ | − | − |

MIC Values of Peptides:

Two (2) peptides, Cecropin P1 and Cecropin A-melittin hybrid, from American Peptides Company, Inc. are tested against strains of *Pseudomnas aeruginosa GSU* # 3 (corneal isolate) and # 9027 (a Gram negative organism), *Staphylococcus aureus* #6538, and *Staphylococcus epidermidis* # 17917. The first two strains are Gram negative organisms. The last two strains are Gram positive organisms. These organisms are chosen because they are the most common etiological agents causing infection in the eye. The peptides are kept at −70° C. until they are ready to be used. The peptide concentrations tested are 20, 16, 8, 4, 2 and 1 μg/ml in Delbeco's Phosphate Buffered Saline (PBS).

The bacteria are harvested, washed twice and adjusted to an O.D. of $10^8$ cells/ml. Cells then are serially diluted and adjusted to about $5 \times 10^5$ cfu/ml. The cells are inoculated into microtiter plates containing serially decreasing peptide concentrations. The inoculum for the bacterial strains are suspended in Mueller Hinton broth, and the final volume in each well is 200 μl. The microtiter plates are incubated at 37° C. for 24 h. The growth is checked as optical density spectrophotometrically in a microtiter plate reader. The O.D. is compared to the blank and to the growth well to determine the MIC.

Minimal inhibition concentrations of peptides against the above four strains are reported in Table 3.

TABLE 3

| Peptide | P. aeruginosa GSU #3 | P. aeruginosa #9027 | S. epidermidis #17917 | S. aureus #6538 |
|---|---|---|---|---|
| Cecropin A-melittin hybrid | >20 μg/ml[1] | 16 μg/mL | 16 μg/mL | 16 μg/mL |
| Cecropin P1 | 20 μg/mL | 20 μg/mL | >20 μg/ml[1] | >20 μg/ml[1] |

[1]highest tested concentration.

Higher concentration is also tested, about 40 μg/ml and 1000 μg/ml. All organisms are killed at 1000 μg/ml, but at 40 μg/ml still the 2 strains of Pseudomnas are not killed by all solutions tested. The same trend is seen with the 2 strains of staph.

The 2 American peptides, Cecropin P1 and Cecropin A-melittin hybrid peptide, are further tested at 20, 10, 5 and 1 μg/ml concentrations. MIC values for those peptides are shown in Table 4 (24 hours) and Table 5 (48 hours). Cecropin A-melittin hybrid peptide has the highest effectiveness against all 4 organisms tested.

TABLE 4

| | Conc against P. aeruginosa GSU #3 | | | | Conc against P. aeruginosa #9027 | | | | Conc against S. epidermidis #17917 | | | | Conc against S. aureus #6538 | | | |
|---|---|---|---|---|---|---|---|---|---|---|---|---|---|---|---|---|
| | 20 | 10 | 5 | 1 | 20 | 10 | 5 | 1 | 20 | 10 | 5 | 1 | 20 | 10 | 5 | 1 |
| Cecropin P1 | + | − | − | − | + | − | − | − | + | − | − | − | + | − | − | − |
| Cecropin A melittin hybrid | + | + | + | − | + | + | + | − | + | + | + | + | + | + | + | − |

TABLE 5

| | Conc against P. aeruginosa GSU #3 | | | | Conc against P. aeruginosa #9027 | | | | Conc against S. epidermidis #17917 | | | | Conc against S. aureus #6538 | | | |
|---|---|---|---|---|---|---|---|---|---|---|---|---|---|---|---|---|
| | 20 | 10 | 5 | 1 | 20 | 10 | 5 | 1 | 20 | 10 | 5 | 1 | 20 | 10 | 5 | 1 |
| Cecropin P1 | − | − | − | − | − | − | − | − | − | − | − | − | − | − | − | − |
| Cecropin A melittin hybrid | + | + | + | − | + | + | + | − | + | + | + | − | + | + | + | − |

We tested further the best peptide Cecropin A melittin hybrid and L-Indolicidin in an MIC assay. The assay is conducted in 10 mM sodium phosphate buffer, the concentration tested are 5, 10, 25 and 50 ppm and the inoculum size is at $5 \times 10^3$. The two peptides show to have a MIC of about 5 ppm.

Cytotoxicity:

Cecropin A melittin hybrid is tested for cytotoxicity at 5, 0.5 and 0.05 μg/ml concentrations. Cytotoxicity of Cecropin A melittin hybrid is evaluated according to the USP Elution Test ("Biological Reactivity Tests, In-Vitro: Elution Test", The United States Pharmacopeial Convention, Inc.). Cell cultures, L929 mammalian fibroblasts (ATCC cell line CCL1, NCTC clone 929), are grown to a near confluent monolayer in 6 well plates (individual wells are 35 mm diameter). A Cecropin A melittin hybrid solution is diluted with serum-supplemented cell culture medium at 25% test solution concentration. The serum-supplemented cell culture medium is prepared by mixing 1000 mL Eagle's sterile minimum essential medium (MEM), 100 mL serum, 10 ml L-glutamine solution and antibiotic-antimycotic solution. Each culture is examined microscopically after 48 hours using trypan blue for the presence of morphological changes, reduction in cell density or cell lysis induced by the Cecropin A melittin hybrid solution. All the 3 concentrations passed the MEM elution and cell growth inhibition and are considered non-cytotoxic.

Indolicidin is tested for cytotoxicity at 5, 0.5 and 0.05 µg/ml concentrations according to the USP Elution Test ("Biological Reactivity Tests, In-Vitro: Elution Test", The United States Pharmacopeial Convention, Inc.), as described above. Cell cultures, L929 mammalian fibroblasts (ATCC cell line CCL1, NCTC clone 929), are grown to a near confluent monolayer in 6 well plates (individual wells are 35 mm diameter). An Indolicidin solution is diluted with serum-supplemented cell culture medium at 25% test solution concentration. The serum-supplemented cell culture medium is prepared by mixing 1000 mL Eagle's sterile minimum essential medium (MEM), 100 mL serum, 10 ml L-glutamine solution and antibiotic-antimycotic solution. Each culture is examined microscopically after 48 hours using trypan blue for the presence of morphological changes, reduction in cell density or cell lysis induced by the Indolicidin solution. All the test concentrations passed the MEM elution test and are considered non-cytotoxic.

Mouse Organ Culture Model:

Using the mouse organ culture model, this assay assesses the ability of a compound to inhibit the binding of *P. aeruginosa* to scarified eyes. Cecropin A melittin hybrid has been tested at three concentrations: 10, 2, and 0.5 µg/ml.

The solutions are tested for their ability to prevent adherence of *P. aeruginosa* (PA) (ATCC# 19660) to scarified mouse cornea. For these studies $1 \times 10^7$ cfu of PA is combined with each of the solutions at each concentration and incubated for 1 h at room temperature. In addition, $1 \times 10^7$ cfu of PA are incubated in PBS for 1 h at room temperature as a control. Following this incubation period, the PA are washed twice to remove the peptide solutions. For each washing step, the cultures are centrifuged at 6,000 rpm for 10 min and pellets are resuspended in 1.0 ml of PBS.

Mouse corneas are scarified under a stereoscopic microscope at 40× magnification. The corneal surface of the eyes is incised with three parallel one-mm wounds. The eyes are then enucleated and placed into sterile culture wells containing 2 ml of MEM.

A 5.0 µl aliquot of each bacterial suspension is delivered onto the surface of the cornea. Eyes are routinely incubated in vitro for 1 h at 37° C. at 95% $O_2$ (5% $CO_2$) after bacterial application. Scanning electron microscopy (SEM) is used to quantitate adherent bacteria.

To determine the efficacy of the peptide, the numbers of bacteria at each concentration is compared from 2 separate identical experiments to the PBS control, $p \leq 0.05$ is considered significant. There is a slight reduction at 0.5 µg, but significant difference in adherence at 2 and 10 µg from the control. The values for the bacteria adhered at 0.5 µg is 42.4 and 32.6 for the PBS control and the peptide solution respectively. At 2 µg, it is 42.4 and 15.8 for the PBS control and the peptide solution respectively. At 10 µg, it is 42.4 and 5.8 for the PBS control and the peptide solution respectively.

EXAMPLE 2

Antimicrobial Contact Lens Coatings

This example illustrates antimicrobial coatings, comprising Cecropin A melittin Hybrid or Indolicidin as an antimicrobial agent, which are formed on soft contact lenses made of a fluorosiloxane hydrogel material, lotrafilcon A.

Preparation of Coating Solutions

Polyacrylic acid (PM) solution. A solution of polyacrylic acid (PM) having an averaged molecular weight of about 90,000 is prepared by dissolving a suitable amount of PAA in water to have [PAA]=0.001M. PAA concentration is calculated based on the repeating unit in PAA. Once dissolved, the pH of the PM solution is adjusted to a desired value.

Poly(allylamine hydrochloride) (PAH) solution. A solution of poly(allylamine hydrochloride) (PAH) having an averaged molecular weight of about 60,000 is prepared by dissolving a suitable amount of the material in water to form a 0.001M PAH solution. PAH concentration is calculated based on the repeating unit in PAH. Once dissolved, the pH of the PAH solution is adjusted to a desired value.

Preparation of Contact Lenses Having Antimicrobial LbL Coatings

The contact lenses, made of a fluorosiloxane hydrogel material, lotrafilcon A, are dipped in a PM solution (0.001M, pH2.5) for 30 min, rinsed with ultra-pure water, then dipped in a PAH solution (0.001M, pH7.5) for 5 minutes, rinsed with ultra-pure water for 1 minute. Three more bilayers are added by alternatively dipping in the solutions of PAA (0.001M, pH 3.5) and PAH (0.002M, pH 7.5), with a rinse step in-between. The contact lenses with four bilayers of polyelectrolytes is dipped in the PM solution (0.001M, pH 3.5) and rinsed with ultra-pure water for 1 minute. A total of 4½ bilayers (PAA/PAH/PAA/PAH/PAA/PAH/PAA/PAH/PAA) are built on each contact lens. The lenses are then packaged in saline and sterilized.

The lenses having an above-described LbL coating are placed in an EDC/SNHS solution (pH 9.0 and containing: a 100 µg/mL solution of either cecropin melittin hybrid or Indolocidin; 10 mg/mL EDC; and 22 mg/mL sulfo-NHS) overnight with gently rocking. The lenses are then removed and rinsed in distilled water.

The covalent coupling of peptides to the lens surface is qualitatively checked via coomassie blue staining of the lens. Each lens is soaked in 1 mL of 0.2% w/v Coomassie brilliant blue R250 for 1 hour. The coomassie stain is made up in destaining solution (5:5:1; methanol:Milli-Q water:acetic acid). The lenses are then placed in individual cages and placed in 500 mL of destaining solution until the uncoated lenses (negative control) are clear. Coomassie blue staining has a detection limit of 2 µg of protein/lens. The results show that a considerable amount of Cecropin A melittin hybrid is present on the lens surface. Indolicidin is also present in detectable quantities, however, not as much as Cecropin. The observed difference may be explained by the difference in the amount of lysine groups available on each peptide between Cecropin A melittin and Indolicidin. Cecropin A melittin hybrid is a 15-residue peptide. Indolicidin is a 13-residue peptide. Cecropin has 5 lysines whereas Indilocidin has only one lysine.

EXAMPLE 3

Antimicrobial Activity of Peptide Soaked or Adsorbed and not Covalently Bound Lenses NewVues soaked lenses in Cecropin A melittin Hybrid at 1 mg/ml concentration is challenged in $1\times10^4$/ml of *P. aeruginosa* # 3 in PBS versus unsoaked NewVues for overnight at 37° C. while shaking. After incubation, the lenses are washed five times in three successive cups of 150-ml volume of PBS to remove loosely bound bacteria. Lenses are placed each in 10 ml-vial saline, sonicate for 6 minutes and vortexed. Aliquots of 100 µl are serially diluted, plated out on TS agar. Plates are incubated for 24-48 h at 37° C., and viable bacteria are counted.

There is about 90% reduction in bacterial adherence from NewVues soaked in Cecropin-A melittin hybrid as compared to the control lens NewVues unsoaked.

EXAMPLE 4

Antimicrobial Activity of Contact Lenses Having Antimicrobial Peptide Covalently Attached to the Surface Thereof Lenses having an antimicrobial coating and covalently coated with indolicidin and with Cecropin A melittin hybrid (Example 2) are tested against the control lenses. 200 µl of $10^4$ cfu/ml of *P. aeruginosa* #3 in PBS is placed on the surface of the lens. Incubate at 25° C. for overnight. Aspirate 100 µl out of the lens, serially dilute and plate out.

About 50% reduction of bacteria recovered from the lenses as compared to the control lens. This shows antimicrobial activity of peptides on the surface of the lens.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A contact lens comprising a core material which is a silicone-containing hydrogel material and an antimicrobial LbL coating that is not covalently attached to the core material, wherein the antimicrobial LbL coating includes:
    (a) a polyelectrolyte LbL coating and an peptide layer of one or more antimicrobial peptides,
    wherein the polyelectrolyte LbL coating is composed of
        (i) at least one layer of a first polyionic material, or
        (ii) at least one layer of the first polyionic material and at least one layer of a second polyionic material having charges opposite of the charges of the first polyionic material,
    wherein said first and second polyionic materials, independently of each other, have functional groups which provide reactive sites, and wherein the peptide layer of one or more antimicrobial peptides are covalently attached to the LbL coating through the reactive sites
    (b) wherein the antimicrobial LbL coating imparts to the core material an increased surface hydrophilicity.

2. A contact lens of claim 1, wherein said one or more antimicrobial peptides are selected from the group consisting of Cecropin A melittin hybrid, indolicidin, lactoferricin, Defensin 1, Bactenecin (bovin), Magainin 2, mutacin 1140, functionally equivalent or suprior analogs thereof, and mixtures thereof.

3. A contact lens of claim 1, wherein said one or more antimicrobial peptides are selected from the group consisting of Cecropin A melittin hybrid and indolicidin.

4. A contact lens of claim 2, wherein the medical device comprises a polyelectrolyte LbL coating and an peptide layer of one or more antimicrobial peptide, wherein the polyelectrolyte LbL coating is composed of (i) at least one layer of a first polyionic material or (ii) at least one layer of the first polyionic material and at least one layer of a second polyionic material having charges opposite of the charges of the first polyionic material, wherein said first and second polyionic materials, independently of each other, have functional groups which provide reactive sites, and wherein the peptide layer of one or more antimicrobial peptides are covalently attached to the LbL coating through the reactive sites.

5. A contact lens of claim 4, wherein one of the first and second polyionic materials is a polyanionic material and the other is a polycationic material, wherein the polyanionic material is selected from the group consisting of polyacrylic acid, polymethacrylic acid, poly(thiophen-3-acetic acid), poly(4-styrenesulfonic acid), PAMAM dendrimers, PAAm-co-PAA, PVP-co-PAA, hyaluronic acid, glycosaminoglycanes, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides, derivatives thereof and mixtures thereof, wherein the polycationic material is selected from the group consisting of poly(allylamine hydrochloride), poly(ethyleneimine), poly(vynylbenzyltriamethylamine), polyaniline, polypyrrole, poly(pyridinium acetylene), polyquat, polyaminoamide, poly-ε-lysine, albumin or collagen, aminoalkylated polysaccharides, derivatives thereof and mixtures thereof.

* * * * *